(12) United States Patent
Boone et al.

(10) Patent No.: US 9,265,923 B2
(45) Date of Patent: Feb. 23, 2016

(54) ANTISEPTIC APPLICATOR

(75) Inventors: Kyle W. Boone, El Paso, TX (US); Manuel Guzman, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 587 days.

(21) Appl. No.: 13/458,642

(22) Filed: Apr. 27, 2012

(65) Prior Publication Data

US 2013/0287471 A1    Oct. 31, 2013

(51) Int. Cl.
*A61M 35/00* (2006.01)
*A61F 13/40* (2006.01)

(52) U.S. Cl.
CPC .................................... *A61M 35/006* (2013.01)

(58) Field of Classification Search
CPC .. A61M 35/00; A61M 35/003; A61M 35/006
USPC ......... 401/132–135, 261, 263, 264, 205, 207; 604/2, 3; 215/213, 254
See application file for complete search history.

(56) References Cited

U.S. PATENT DOCUMENTS

| | | | | |
|---|---|---|---|---|
| 3,082,468 A | * | 3/1963 | Wattles | 401/132 |
| 3,369,267 A | * | 2/1968 | Friedland et al. | 401/132 |
| 3,896,808 A | * | 7/1975 | Szpur | 604/3 |
| 3,981,304 A | * | 9/1976 | Szpur | 604/3 |
| 4,148,318 A | * | 4/1979 | Meyer | 604/3 |
| 4,190,175 A | * | 2/1980 | Allen | 220/270 |
| 4,925,667 A | * | 5/1990 | Fellows et al. | 401/132 |
| 6,315,482 B1 | * | 11/2001 | Girardot et al. | 401/261 |
| 6,325,563 B1 | * | 12/2001 | Matechuk | 401/261 |
| 6,439,792 B1 | * | 8/2002 | Beguin et al. | 401/261 |
| 7,651,290 B2 | * | 1/2010 | Bauer et al. | 401/133 |
| 7,950,864 B2 | * | 5/2011 | Bauer et al. | 401/132 |
| 8,210,764 B2 | * | 7/2012 | Holowecky | 401/132 |
| 8,485,356 B2 | * | 7/2013 | Thorne et al. | 604/3 |
| 8,641,310 B2 | * | 2/2014 | Pennella | 401/133 |
| 2006/0251464 A1 | * | 11/2006 | Bauer et al. | 401/205 |
| 2009/0320856 A1 | * | 12/2009 | Brewer et al. | 604/309 |
| 2010/0286637 A1 | * | 11/2010 | Cable et al. | 604/310 |

* cited by examiner

*Primary Examiner* — David Walczak
*Assistant Examiner* — Bradley Oliver
(74) *Attorney, Agent, or Firm* — Arent Fox LLP

(57) ABSTRACT

An applicator assembly includes a container having a proximal end, a distal end, and an interior portion defining a chamber, an application member attached to the distal end of the container, and a tearable solution reservoir disposed within the chamber, the tearable solution reservoir comprising a tearing member, wherein actuating the tearing member to tear the tearable solution reservoir brings the container, the tearable solution reservoir, and the application member into fluid communication with each other.

19 Claims, 3 Drawing Sheets

ANTISEPTIC APPLICATOR

BACKGROUND

1. Field

The present disclosure relates to an antiseptic applicator and method of use thereof, and more particularly, to an antiseptic applicator that requires the application of force to actuate release of a sealed solution, preferably an antimicrobial solution, from a self-contained reservoir toward a material arranged at a distal end of the applicator for receiving the solution.

2. Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

Conventional antiseptic applicators, as described above, often require special packaging and/or handling during shipping and prior to use. For example, with the puncture type applicators, preventive measures are required to prevent an inadvertent push against either end of the device that may result in the puncturing of the sealed container and the premature discharge of the solution. A user must often use both hands to effectively overcome the preventive measures and activate the applicator for use. In addition, conventional antiseptic applicators often rely on the exertion of pressure on the walls of an applicator, for example, to break a frangible ampoule or squeeze the solution from the container toward an application material. The use of frangible ampoules requires special care to avoid breaking as a result of inadvertent pressure or dropping during shipping or prior to use. Furthermore, the components of a conventional applicator, such as the broken ampoule or the puncture spike, often impede the free flow of the solution from the container. There exists a need in the field for a novel antiseptic applicator that avoids the complications associated with conventional applicators, especially an applicator that will allow for effective one hand actuation and application of a solution without impediments to the free flow of the solution from the container to the application material.

SUMMARY

In accordance with aspects of the present invention, an applicator assembly may include a container having a proximal end, a distal end, and an interior portion defining a chamber, an application member attached to the distal end of the container, and a tearable solution reservoir disposed within the chamber, the tearable solution reservoir comprising a tearing member, wherein actuating the tearing member to tear the tearable solution reservoir brings the container, the tearable solution reservoir, and the application member into fluid communication with each other.

In accordance with another aspect of the present invention, the container further comprises an opening, wherein the tearing member is accessible via the opening.

In accordance with other aspects of the present invention, the tearable solution reservoir further comprises at least one tear line abutting the tearing member.

In accordance with another aspect of the present invention, the tearable solution reservoir further comprises a locking mechanism and the container further comprises a projecting element, wherein mating the projecting element and the locking mechanism prevents movement of the tearable solution reservoir within the container.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
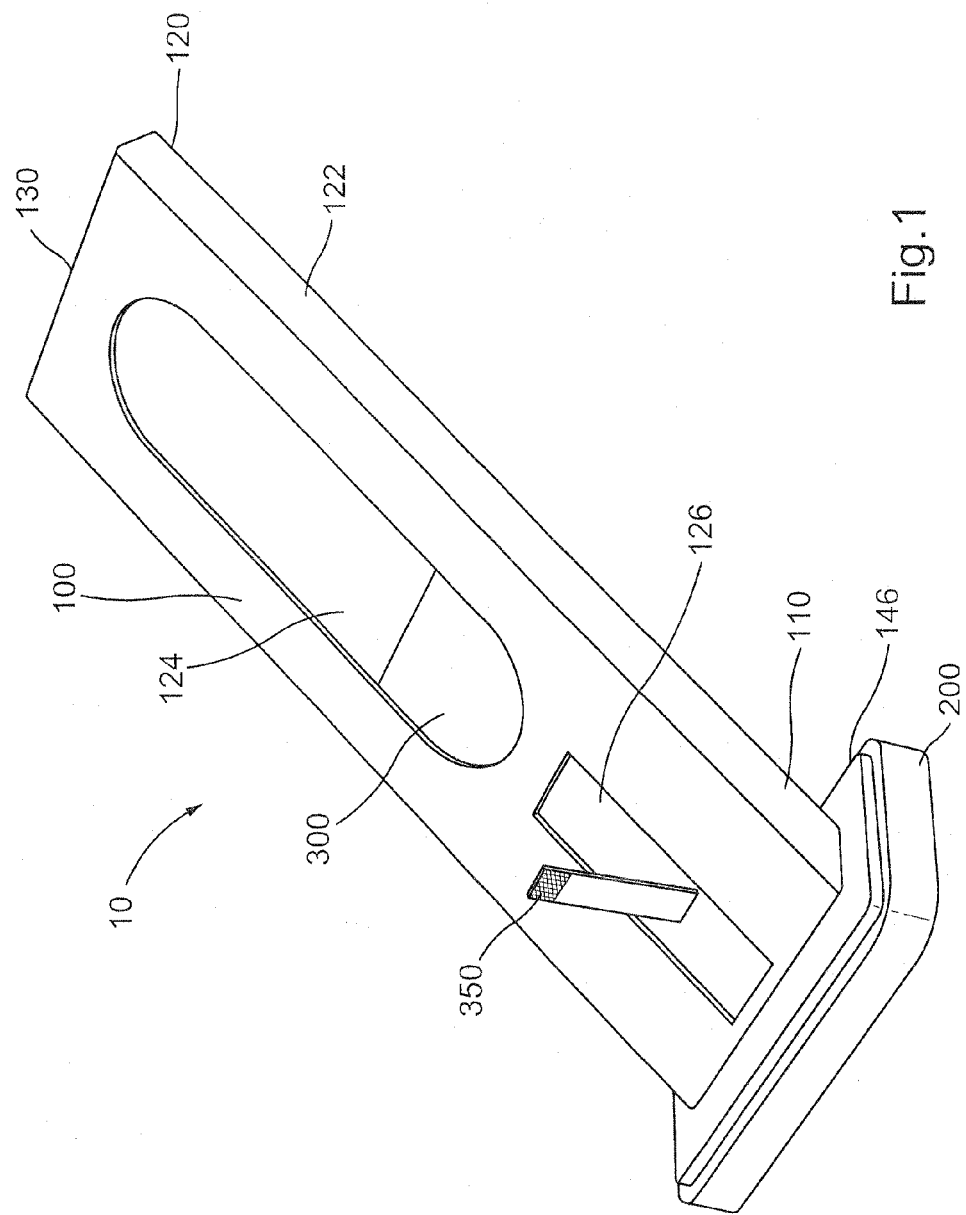
FIG. 1 is a perspective view of an antiseptic applicator, in accordance with certain aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 2:
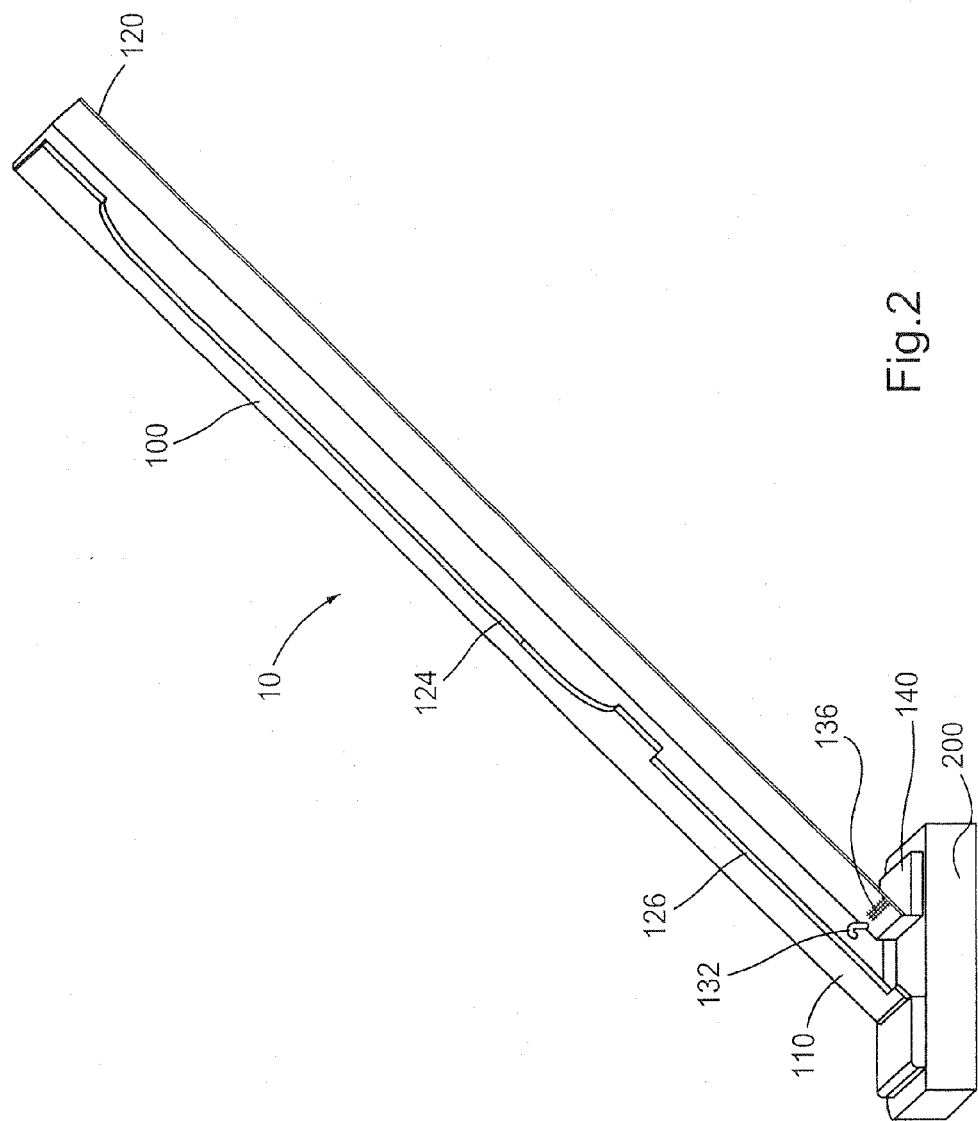
FIG. 2 is a side cutaway view of the antiseptic applicator of FIG. 1, in accordance with certain aspects of the present invention.

The antiseptic applicator may be compact and ergonomically designed. As shown in FIGS. 1 and 2, an antiseptic applicator 10 may comprise a substantially hollow container 100, which preferably may be rectangular in shape, an application member 200 mounted to a distal end 110 of the container 100, and a tearable solution reservoir 300 receivable in the container 100. The application member 200 preferably may be rectangular in shape to correspond with the container 100. While a rectangular geometry is illustrated, it is within the scope of the invention that any suitable geometry may be implemented, such as a cylinder. The container 100 may integrally formed with the application member 200.

The application member 200 may comprise a foam sponge material, for example, or any suitable material that allows the controlled application of the contained solution from the container 100 to a surface external to the applicator 10. The material chosen may be porous with a particular soak rate, for example, or may be provided with structural features, including slits or apertures, to direct and control the flow rate of the solution through the application member 200. The applicator may be configured to have a mounting flange 140 at the distal end 110. The mounting flange 140 provides a surface for affixing the application member 200 to the container 100.

The container 100 is preferably a self-contained structure, formed of a suitable material, such as a plastic, e.g., a high-density polyethylene plastic, that is flexible, yet resistant to deformation and chemical leaching. As shown in FIGS. 1 and 2, the container 100 may include a first opening 124 and a second opening 126 provided in a front surface of the container 100. The function of the openings is described below. The container 100 may be generally hollow so as to receive a tearable solution reservoir 300. The distal end 110 of the container 100 may include a projecting element 132, such as a hook and/or a knurled surface, to mate with the tearable solution reservoir 300. The projecting element can be disposed on any portion of the internal surface of the container that allows the projecting element to mate with the tearable solution reservoir.

Figure 3:
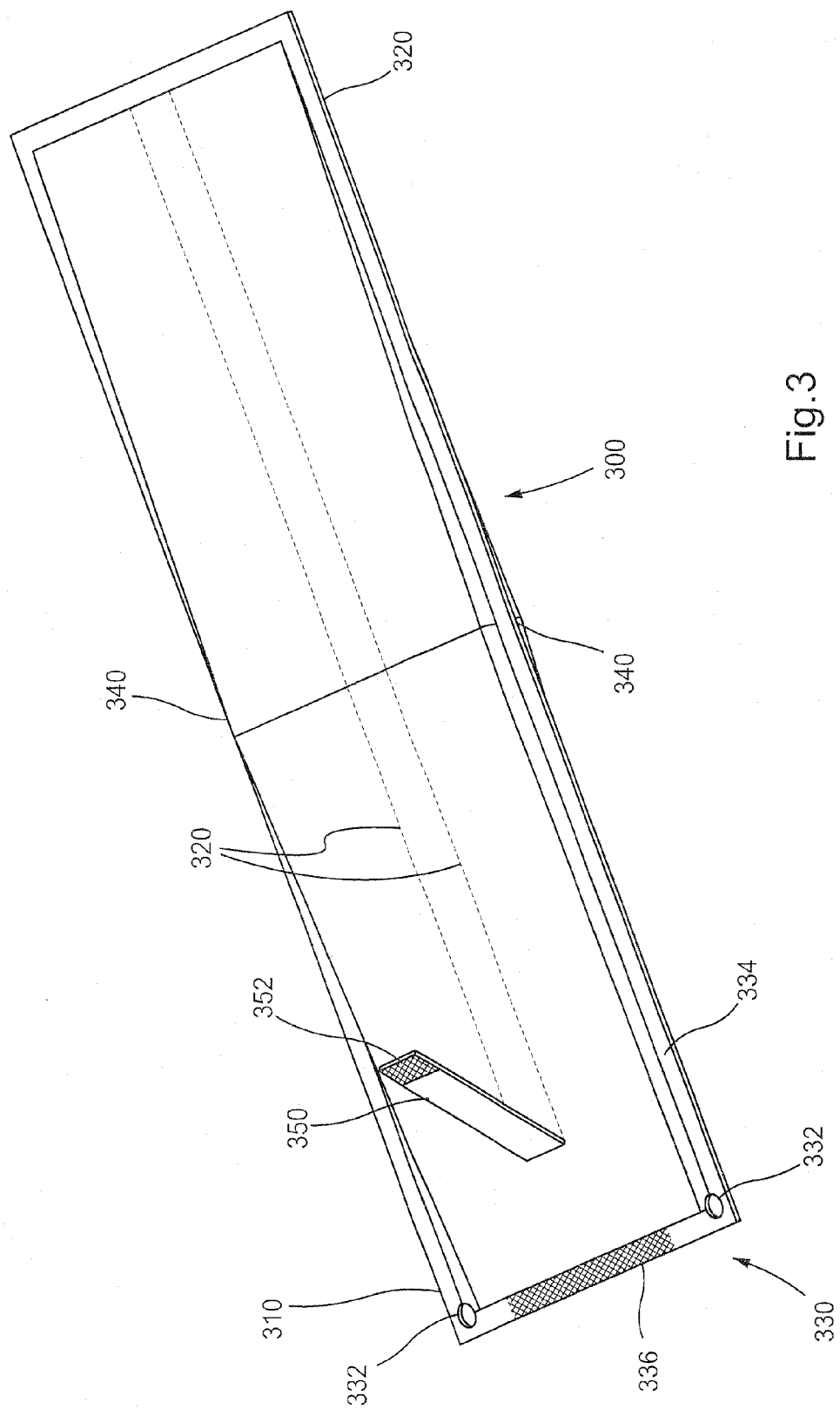
FIG. 3 is a perspective view of a tearable solution reservoir used in combination with the antiseptic applicator of FIG. 1.

FIG. 3 shows a perspective view of the tearable solution reservoir 300. The tearable solution reservoir 300 comprises material that is capable of being torn when a tearing force is applied, such as by a user's hand, to allow tearing of the tearable solution reservoir 300 when the release of the solution is desirable. For example, the tearable solution reservoir 300 may comprise a metal foil or a plastic material. The tearable solution reservoir 300 may contain various liquids such as antiseptics or medicaments, chemical compositions, cleansing agents, cosmetics, or the like, and preferably an antimicrobial liquid or gel composition, for antiseptic application to a patient prior to surgery. The tearable solution reservoir 300 is designed to withstand various heat and chemical sterilization techniques, which may be performed sequentially with a solution filling process, in accordance with techniques that are well known in the art, such as a blow-fill-seal technique. Preferable antimicrobial agents contained in the tearable solution reservoir include octenidine salts, chlorhexidine salts, alcohol, aldehyde, anilide, diamidine, halogen-releasing agent, silver compound, peroxygen, and/or phenols. A preferable octenidine salt includes octenidine dihydrochloride and a preferable chlorhexidine salt includes chlorhexidine gluconate.

As shown in FIG. 2, the container 100 may comprise an elongated rectangular prism formed by the sidewall 122. A closing member 130 may be provided at the proximal end 120. The closing member 130 may be integrally formed with the container 100 or, for example, may be a separate component connected to the container, such as an end cap for mating via a threaded connection with the proximal end 120, or a plug that may be press fit or heat welded to the container 100, for sealing shut the open proximal end 120. Thus, in accordance with certain aspects of the present invention, the tearable solution reservoir 300 may be inserted into the container 100 through the open proximal end 120 of the container 100 prior to the container 100 being sealed shut with the closing member 130.

As shown in FIGS. 1 and 2, the sealed container 100 may be attached or integrally formed with the application member 200. The tearable solution reservoir 300, being sealed prior to being placed into the container 100, prevents the solution present in the tearable solution reservoir 300 from flowing into the application member 200. Thus, prior to tearing the solution reservoir 300, the applicator 10 does not dispense the solution.

As shown in FIGS. 1 and 3, the tearable solution reservoir 300 includes a tearing member 350, such as a tab, which may be attached a surface of the tearable solution reservoir 300. The tearing member 350 may include a grip surface 352, such as a knurled surface, to assist the user in holding onto the tearing member. The tearing member 350 may be attached to a portion of the tearable solution reservoir 300 such that, when inserted into the container 100, the tearing member is accessible through the opening 126. The opening 126 allows an operator of the device to grip the tearing member 350 through the container 100. The portion of the tearable solution reservoir 300 that is visible through the opening 126 may include printed instructions indicating which direction the tearing member 350 should be pulled to release the solution. Before the tearable solution reservoir 300 is torn by pulling the tearing member 350, the solution is prevented from entering into the application member 200. The tearing member 350 may be pivotable about the point where the tearing member connects to the tearable solution reservoir 300 to allow an operator to pivot the tearing member 350 to a position that allows for easier tearing. The tearing member 350 may be disposed anywhere on tearable solution reservoir 300 that would be accessible through the window 126.

The tearable solution reservoir 300 may further include one or more tear lines 320 to assist in tearing the tearable solution reservoir 300. In an aspect of the invention, the tear lines 320 may be partial perforations to avoid leakage of the solution contained within the tearable solution reservoir 300. For example, the partial perforation may include spaced apart points of reduced thickness of the material. As shown in FIG. 3, two tear lines 320 may be included. Each tear line may meet the tearing member 350 at the point where the tearing member contacts the tearable solution reservoir 300 and may extend toward a proximal end 320. Thus, while the container 100 shown in FIG. 1 does not include a continuous opening, it is within the scope of the invention that a continuous opening may be implemented to allow tearing along substantially the entire length of the tearable solution reservoir. The tear lines 320 may extend to the proximal end 320 to provide the user the option of tearing the tearable solution reservoir to the proximal end 320. Alternatively, the tear lines may extend towards the distal end 310, or may extend laterally towards the sides 340 of the tearable solution reservoir.

The tearable solution reservoir 300 may further include a locking mechanism 330 disposed towards the distal end 310 for locking the tearable solution reservoir into the container 100 and restricting movement of the tearable solution reservoir. In an aspect of the present invention, the locking mechanism 330 may comprise one or more insertion holes 332. The one or more insertion holes 332 may comprise through holes that pass through a portion of the tearable solution reservoir 300 that does not comprise solution, such as perimeter edge 334. The locking mechanism 330 may be placed to align with the projecting element 132 such that when the tearable solution reservoir 300 is placed within the container 100, the projecting element 132 will mate with the locking mechanisms 330. For example, a hook if the container may mate with an insertion hole of the tearable solution reservoir. The container may include more than projecting element such that each locking mechanism corresponds to one projecting element. The locking mechanism 330 may alternatively or additionally include a knurled surface 336, optionally positioned to mate with a knurled surface 136 of the container 100, if present. The knurled surfaces 136, 336 may be positioned and angled such that when the tearable solution reservoir is placed within the container 100, the knurled surfaces 136, 336 mate, thereby preventing relative movement of the tearable solution reservoir. While the knurled surface 336 is shown in FIG. 3 as being on the top surface of the tearable solution reservoir 300, the knurled surface may also be disposed on the opposite surface. It is within the scope of the invention that the locking mechanism may include either one or both of the insertion holes and knurled surface.

A fluid metering device, such as a pledget, for example, may optionally be provided in the fluid chamber to further control and/or direct the flow of solution from the container 300 when the assembly 10 is in use.

To activate the applicator 10 and release the solution, a user may grasp the container 100 and the tearing member 350, and then pull the tearing member 350 to separate the tear lines 320. The locking mechanism 330, when mated with the corresponding features in the container 100, holds the tearable solution reservoir 300 in place, thereby allowing movement of the tearing member 350 relative to the tearable solution reservoir 300. The pulling force of tearing member 350 will cause the tearable solution reservoir 300 to tear.

The tearing of the tearable solution reservoir 300 provides fluid communication between the tearable solution reservoir 300, the container 100, and the application member 200. Gravity will cause the solution to flow out of the torn solution reservoir 300 and into the application member 200. After the solution has been discharged, the operator can simply load a new tearable solution reservoir 300 and repeat the above steps. Thus, the present invention provides for a re-usable container 100.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
   a container having a proximal end, a distal end, and an interior portion defining a chamber;
   a foam application member attached to the distal end of the container; and
   a solution reservoir disposed within the chamber, the solution reservoir comprising:
   a tearable body for containing a solution; and
   a tearing member attached to the body,
   wherein actuating the tearing member to tear the tearable body brings the container, the solution reservoir, and the application member into fluid communication with each other.

2. The applicator assembly of claim 1,
   wherein the container further comprises an opening, and
   wherein the tearing member is accessible via the opening.

3. The applicator assembly of claim 1, wherein the tearable body further comprises at least one tear line abutting the tearing member.

4. The applicator assembly of claim 1,
   wherein the solution reservoir further comprises a locking mechanism,
   wherein the container further comprises a projecting element mateable with the locking mechanism, and
   wherein mating the projecting element with the locking mechanism prevents movement of the solution reservoir within the container.

5. The applicator assembly of claim 4,
   wherein the projecting element comprises one or more of a hook and a first knurled surface, and
   wherein the locking mechanism comprises one or more of an insertion hole and a second knurled surface.

6. The applicator assembly of claim 5,
   wherein the hook is mateable with the insertion hole, and
   wherein the first knurled surface is mateable with the second knurled surface.

7. The applicator assembly of claim 3, wherein the at least one tear line comprises a partial perforation, thereby preventing fluid from leaking through the tear line.

8. The applicator assembly of claim 1, wherein the tearing member is a tab comprising a knurled surface.

9. The applicator assembly of claim 4,
   wherein the projecting member is disposed on an inner surface of the container at the distal end of the container, and
   wherein the locking mechanism is disposed on a perimeter of the solution reservoir at the distal end of the solution reservoir.

10. The applicator assembly of claim 1, wherein the container further comprises a removable closing member at the proximal end of the container allowing removal of the solution reservoir.

11. The applicator assembly of claim 3, wherein the at least one tear line extends from the tearing member toward a distal end, a proximal end, or a side portion of the tearable body.

12. The applicator assembly of claim 1, wherein foam application member has a perimeter larger than a perimeter of the distal end of the container.

13. The applicator assembly of claim 1, further comprising a mounting flange at the distal end of the container.

14. The applicator assembly of claim 13, wherein the foam application member is affixed to the mounting flange, and wherein the application member has a perimeter larger than the perimeter of the mounting flange.

15. The applicator assembly of claim 1, wherein the foam application member comprises a porous material having a soak rate sufficient to distribute the solution through the application member.

16. The applicator assembly of claim 1, wherein the solution comprises an antiseptic solution.

17. The applicator of claim 16, wherein the antiseptic solution comprises an antimicrobial agent selected from the group consisting of octenidine salts, chlorhexidine salts, alcohols, aldehydes, anilides, diamidines, halogen-releasing agents, sliver compounds, peroxygens, and phenols.

18. The applicator assembly of claim 16, wherein the antiseptic solution comprises an octenidine salt or a chlorhexidine salt.

19. An applicator assembly comprising:
a container having a proximal end, a distal end, an interior portion defining a chamber, and a projecting element, the projection element comprising one or more of a hook and a first knurled surface;
an application member attached to the distal end of the container; and
a tearable solution reservoir disposed within the chamber, the tearable solution reservoir comprising a tearing member and a locking mechanism mateable with the projecting element, the locking mechanism comprising one or more of an insertion hole and a second knurled surface,
wherein mating the projecting element with the locking mechanism prevents movement of the tearable solution reservoir within the container, and
wherein actuating the tearing member to tear the tearable solution reservoir brings the container, the tearable solution reservoir, and the application member into fluid communication with each other.

* * * * *